United States Patent [19]
Engelhardt et al.

[11] Patent Number: 4,647,588
[45] Date of Patent: Mar. 3, 1987

[54] 2-(SUBSTITUTED SULFAMYL)-6-NITROBENZOIC ACID AMIDES AND PHARMACEUTICAL COMPOSITIONS

[75] Inventors: Edward L. Engelhardt, Gwynedd Valley; Walfred S. Saari, Lansdale, both of Pa.

[73] Assignee: Merck & Co., Inc., Rahway, N.J.

[21] Appl. No.: 795,569

[22] Filed: Nov. 6, 1985

Related U.S. Application Data

[63] Continuation-in-part of Ser. No. 716,886, Mar. 27, 1985, abandoned.

[51] Int. Cl.$^4$ .................... A61K 31/18; C07C 143/78
[52] U.S. Cl. ..................................... 514/603; 560/13; 562/430; 564/87; 514/535; 514/562
[58] Field of Search .......................... 560/13; 562/430; 564/87; 514/535, 562, 603

[56] References Cited

U.S. PATENT DOCUMENTS 3,017,427 1/1962 Hamor ................................. 560/13
4,113,463 9/1978 Oshio et al. ......................... 562/430

Primary Examiner—Robert W. Ramsuer
Attorney, Agent, or Firm—Thomas E. Arther; Roy D. Meredith; Hesna J. Pfeiffer

[57] ABSTRACT 2-(Substituted sulfamyl) derivatives of 6-nitrobenzoic acid wherein at least one of the sulfamyl substituents is a basic substituent selected from amino-(lower alkyl), (lower alkyl)-amino-(lower alkyl), or di(lower alkyl)-amino-(lower alkyl) are disclosed to have activity in increasing the sensitivity of hypoxic tumor cells to therapeutic radiation. Also disclosed are methods of preparing such compounds and pharmaceutical compositions including such compounds.

3 Claims, No Drawings

2-(SUBSTITUTED SULFAMYL)-6-NITROBENZOIC ACID AMIDES AND PHARMACEUTICAL COMPOSITIONS

CROSS REFERENCE TO OTHER APPLICATIONS

This application is a continuation-in-part of application Ser. No. 716,886 of Walfred S. Saari filed Mar. 27, 1985, now abandoned.

BACKGROUND OF THE INVENTION

This invention relates to 2-(substituted sulfamyl)-6-nitrobenzoic acids, esters, amides and N-substituted amides thereof used as sensitizers of hypoxic tumor cells to therapeutic radiation. It also relates to the process of preparing such compounds starting with a 2-chlorosulfonyl-6-nitro benzoate ester and aminating said 2-chlorosulfonyl benzoate ester to produce the corresponding 2-(substituted sulfamyl)-6-nitrobenzoic ester, and converting said ester to the substituted carboxamide.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, and are believed to have a more favorable therapeutic ratio.

DETAILED DESCRIPTION OF THE INVENTION

The compositions of the present invention are nitrobenzenesulfonamide compounds of the formula

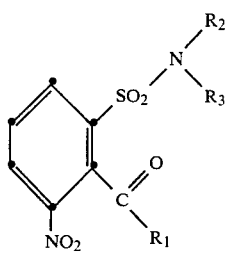

wherein $R_1$ is hydroxy, hydroxy-(lower alkoxy), lower alkoxy, allyloxy, amino, monoalkylamino, dialkylamino, hydroxyalkylamino, di(hydroxyalkyl)-amino, or allylamino.

$R_2$ and $R_3$ are each separately hydrogen, lower alkyl from 1-4 carbon atoms, hydroxy-(lower alkyl), allyl, amino-(lower alkyl), (lower alkyl)-amino-(lower alkyl), di-(lower alkyl) amino-(lower alkyl), (hydroxyalkyl)-amino(loweralkyl), (hydroxyalkyl)-alkylamino(loweralkyl) or di(hydroxyalkyl)-amino(loweralkyl) provided that at least one of $R_2$ and $R_3$ contains a basic substituent selected from amino-(lower alkyl), (lower alkyl)-amino-(lower alkyl), di(lower alkyl)amino-(lower alkyl), (hydroxyalkyl)-amino(loweralkyl), (hydroxyalkyl)-alkylamino(loweralkyl) or di(hydroryalkyl)-amino(-loweralkyl).

The 2-(substituted sulfamyl) derivatives of 6-nitrobenzoic acid, ester and amide compounds of the present invention are prepared in the following manner:

A substituted nitrobenzoate ester or nitrobenzamide having a 2-chlorosulfonyl substituent in an aprotic solvent such as tetrahydrofuran, dioxane, dimethoxyethane, or chloroform is treated with at least an equimolar amount of an amine of the formula

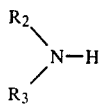

wherein $R_2$ and $R_3$ are as described hereinabove.

It is preferred to carry out the reaction in the presence of a base in sufficient amount to neutralize the hydrogen chloride formed in the course of the reaction. The base utilized may be a tertiary amine such as triethylamine or pyridine. On the other hand the same results may be produced by adding at least twice the molar amount of reactant amine theoretically required. In this event, the reactant amine is utilized both to form the sulfonamide and to neutralize the hydrogen chloride formed in the amination reaction.

The temperature at which the reaction is carried out is not critical and may vary from 0°-100° C. or at the reflux temperature of the solvent, if under 100° C. The reaction temperature is preferably maintained at about 0°-25° C. for a period of 1-24 hours. The amination reaction may be formulated as follows:

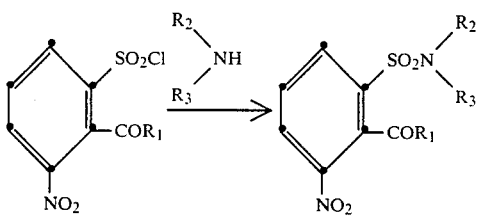

wherein $R_1$, $R_2$ and $R_3$ are as defined hereinabove.

The starting materials for the process are either known or are readily prepared from the known 2-amino-6-nitrobenzoic acid by a process of esterification followed by diazotization of the amino group and treating the formed diazonium compound with $SO_2$ in the presence of $CuCl_2$ whereby the desired starting 2-chlorosulfonyl-6-nitrobenzoate ester is formed.

The ester derivatives of this invention may also be prepared by esterification of a carboxylic acid of formula I ($R_1$=OH). Established methods for the esterification of carboxylic acids containing basic groups may be used. These include reaction with diazoalkanes or with alcohols under strongly acidic conditions.

The benzamide derivatives of this invention may be prepared by reaction of a 2-monosubstituted sulfamyl-6-nitrobenzoate ester of formula III or a 2-substituted-4-nitro-2H-1,2-benzisothiazol-3-one 1,1-dioxide of formula IV with at least one equivalent of ammonia or a mono- or dialkyl-substituted amine of formula II.

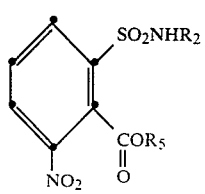

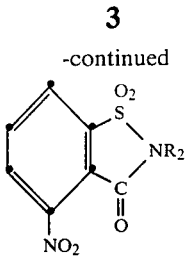

In formulas III and IV, R$_2$ is as described hereinabove and R$_5$ is either lower alkyl or hydroxy-(lower alkyl). The reaction is carried out in a suitable solvent such as a lower aliphatic alcohol or a polar aprotic solvent such as dimethylformamide, dimethylsulfoxide or others such as tetrahydrofuran, glyme, diglyme, chloroform or methylenechloride. The reaction temperature is not critical and may vary from 0°–100° C., preferably from about 25°–50° C. for a period of 1 to 10 days. When low boiling amines are used, the reaction may be run in a sealed vessel.

The compounds of this invention may also be prepared by alkylation of an amine with an amide or ester of formula V wherein R$_1$ and R$_2$ are as defined hereinabove and R$_6$ is an alkylating moiety such as haloalkyl, alkylsulfonyloxyalkyl or arylsulfonyloxyalkyl.

The reaction is carried out in a suitable aprotic solvent such as dimethylformamide, acetonitrile or the like. The reation temperture may vary from 50° C. to the boiling point of the solvent for a period of 1 to 10 days. When low boiling amines are used, the reaction may be run in a sealed vessel. It is preferred to carry out the reaction in the presence of a base in sufficient amount to neutralize the acid formed in the course of the reaction. The base utilized may be a tertiary amine such as a trialkylamine or pryidine. Alternatively, at least twice the molar amount of reactant amine theoretically required may be used. In this event, the reactant amine is utilized both to form the desired product and to neutralize the acid formed in the aminations reaction.

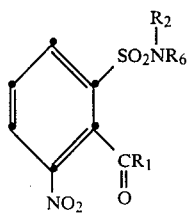

The alkylating agents of formula V are readily prepared from the corresponding alcohols by established methods.

The method of treatment of human patients or domestic animals undergoing radiation treatment of malignant disease processes employs the compounds of the present invention in pharmaceutical compositions that are administered orally or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLE 1

Step A: Methyl 2-Amino-6-nitrobenzoate

A mixture of 2-amino-6-nitrobenzoic acid (11.9 g, 65.3 mmol), methyl p-toluenesulfonate (15.1 g, 81.1 mmol) and triethylamine (6.60 g, 65.3 mmol) in DMF (170 ml) was stirred under N$_2$ at 60° for 18 hours. After removing DMF at 60° and 0.2 mm pressure, the residue was dissolved in ETOAc and washed with a saturated solution of NaHCO$_3$ followed by a saturated aqueous solution of NaCl. The EtOAc extract was dried (Na$_2$SO$_4$), filtered and concentrated under reduced pressure. Flash chromatography over silica gel and elution with 50% toluene-50% CHCl$_3$ gave methyl 2-amino-6-nitrobenzoate (7.6 g, 59.4%), m.p. 105°–107°.

Step B: Methyl 2-Chlorosulfonyl-6-nitrobenzoate

To a suspension of methyl 2-amino-6-nitrobenzoate (7.6 g, 38.7 mmol) in glacial acetic acid (37 ml) and conc. HCl (67 ml), cooled to −5°, was added slowly a solution of sodium nitrite (2.86 g, 41,4 mmol) in H$_2$O (11.2 ml). After addition was complete, the mixture was stirred at −5° to 0° for an additional 30 minutes. During this time, a solution of CuCl$_2$.2H$_2$O (2.45 g) in H$_2$O (8.5 ml) was prepared and added to a cold solution of SO$_2$ (25 g, 0.39 mol) in glacial acetic acid (50 ml). The diazonium salt solution was then added in portions to the cooled SO$_2$—CuCl$_2$ mixture. After stirring in an ice bath for 3 hours, the reaction mixture was allowed to warm to 20°–25° and was stirred at this temperature for 18 hours. The reaction mixture was then poured onto ice (500 g), the precipitated tan solid removed by filtration and dried to give the sulfonyl chloride (9.1 g, 84.3%), m.p. 152°–4°.

EXAMPLE 2

Methyl 2-[N-(2-Dimethylaminoethyl)aminosulfonyl]-6-nitrobenzoate Hydrochloride and 2-[N-(2-Dimethylaminoethyl)aminosulfonyl]-6-nitrobenzoic acid A solution of methyl 2-chlorosulfonyl-6-nitrobenzoate (500 mg, 1.79 mmol) and 2-dimethylaminoethylamine (316 mg, 3.58 mmol) in THF (35 ml) was stirred in an ice bath for 1 hour then at 20°–25° for 18 hours. After removing THF under reduced pressure, the residue was partitioned between saturated $Na_2CO_3$ solution and EtOAc. The organic extract was washed (saturated NaCl solution), dried ($Na_2SO_4$), filtered and concentrated under reduced pressure. Chromatography over silica gel (elution with 5% MeOH-95% $CHCl_3$) gave an oil which when triturated with EtOAc afforded 2-[N-(2-dimethylaminoethyl)aminosulfonyl]-6-nitrobenzoic acid (90 mg, 16%), m.p. 193° decomposed with effervescence.

Treatment of the EtOAc soluble fraction with anhydrous EtOH-HCl and recrystallization from EtOH-EtOAc gave the HCl salt of the methylester (250 mg, 38%), m.p. 170°–173°.

EXAMPLE 3

N,N-Dimethyl-2-[N-(2-dimethylaminoethyl)aminosulfonyl]-6-nitrobenzamide Hydrochloride A solution of methyl 2-[N-(2-dimethylaminoethyl)aminosulfonyl]-6-nitrobenzoate (200 mg, 0.544 mmol) and 0.5 ml of a 40% aqueous dimethylamine solution in methanol (5 ml) was allowed to stand at 20°–25° for 18 hours. After concentrating under reduced pressure, the residue was treated with anhydrous ethanolic hydrogen chloride and recrystallized from MeOH-EtOAc to give the HCl salt m.p. 166°–69°.

EXAMPLE 4

N,N-Dimethyl 2-[N-(2-Dimethylaminoethyl)-N-(2-hydroxyethyl)aminosulfonyl]-6-nitrobenzamide Hydrochloride Step A: N,N-Dimethyl 2-[N-(2-dimethylaminoethyl)-N-(2-(2-tetrahydro-2H-pyranyloxy)ethyl)aminosulfonyl]-6-nitrobenzamide To a suspension of N,N-dimethyl 2-[N-(2-dimethylaminoethyl)aminosulfonyl]-6-nitrobenzamide hydrochloride (347 mg, 0.91 mmol) in DMF (5 ml) under $N_2$ was added 50% NaH (87 mg, 1.82 mmol). After stirring at 20°–25° for 15 minutes until all of the NaH had reacted, a solution of 2-(2-bromoethoxy)tetrahydro-2H-pyran in DMF (2 ml) was added. The solution was stirred at 20°–25° under $N_2$ for 20 hours and then concentrated under reduced pressure to remove most of the DMF. The residue was partitioned between EtOAc and a saturated aqueous solution of NaCl. After drying ($Na_2SO_4$) the EtOAc extract, filtering and concentrating, the residue was chromatographed over silica gel. Elution with 7% MeOH-93% $CHCl_3$ gave 100 mg of product.

Step B: N,N-Dimethyl 2-[N-(2-dimethylaminoethyl)-N-(2-hydroxyethyl)aminosulfonyl]-6-nitrobenzamide Hydrochloride A solution of the tetrahydropyranyl ether (100 mg) in THF (10 ml), $H_2O$ (5 ml) and HOAc (20 ml) was stirred at 50° for 24 hours. After concentrating under reduced pressure, the residue was partitioned between EtOAc and saturated $NaHCO_3$ solution. The EtOAc extract was washed (saturated NaCl solution), dried ($Na_2SO_4$), filtered and concentrated. The crude product was purified by conversion to the HCl salt and recrystallized (MeOH-EtOAc-hexane) to give 32 mg of product, m.p. 162°–64° C. dec.

EXAMPLE 5

N,N-Dimethyl 2-{N-[2-(N-(2-Hydroxyethyl)-N-methylamino)-ethyl]-N-methylaminosulfonyl}-6-nitrobenzamide Hydrogen Oxalate Step A: N,N-Dimethyl 2-[N-(2-Methylsulfonyloxyethyl)-N-methylaminosufonyl]-6-nitrobenzamide A solution of N,N-dimethyl 2-[N-(2-hydroxyethyl)-N-methylaminosulfonyl]-6-nitrobenzamide, prepared as described in Example 9 U.S. Ser. No. 795,564 filed 11-6-85 of Walfred Saari filed on the same date as the present case and incorporated herein by reference, (1.0 g, 3.0 mmol) and methanesulfonyl chloride (0.71 g, 6.2 mmol) in pyridine (10 ml) was stirred at 20°–25° for one day. After concentrating under reduced pressure, the residue was partitioned between ethyl acetate and 1N aqueous HCl. The ethyl acetate extract was washed with water, dried and concentrated. Pure mesylate (1.0 g) was obtained by flash chromatography over silica gel and elution with a 1% methanol-99% chloroform solvent mixture.

Step B: N,N-Dimethyl 2-{N-[2-(N-(2-Hydroxyethyl)-N-methylamino)ethyl]-N-methylaminosulfonyl}-6-nitrobenzamide Hydrogen Oxalate A solution of N,N-dimethyl 2-[N-(2-methylsulfonyloxyethyl)-N-methylaminosulfonyl]-6-nitrobenzamide (0.50 g, 1.2 mmol) and 2-(methylamino)ethanol (0.22 g, 2.9 mmol) in acetonitrile (20 ml) was stirred at reflux for 20 hours. After concentrating under reduced pressure, the residue was partitioned between ethyl acetate and water. The ethyl acetate layer was dried ($Na_2SO_4$), filtered and concentrated. Flash chromatography of the residue over silica gel and elution with 5% methanol-95% chloroform gave 400 mg of pure product as an oil. The hydrogen oxalate salt, mp 159.0°–162.0°, was prepared for analysis.

What is claimed is:

1. A 2-(substituted aminosulfonyl)-6-nitrobenzoic acid amide of the formula

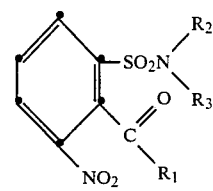

wherein
$R_1$ is amino, monoalkylamino, dialkylamino, hydroxyalkylamino, di(hydroxyalkyl)amino or allylamino;
$R_2$ and $R_3$ are each separately hydrogen, lower alkyl, hydroxy-(lower alkyl), allyl, amino-(lower alkyl), (lower alkyl)-amino-(loweralkyl), di-(lower alkyl)-amino-(lower alkyl), (hydroxyalkyl)amino-(loweralkyl), (hydroxyalkyl)alkylamino-(loweralkyl) or di(hydroxyalkyl)amino-(loweralkyl) provided that at least one of $R_2$ and $R_3$ contain a basic substituent selected from (hydroxyalkyl)-amino-(loweralkyl), (hydroxyalkyl)-alkylamino-(loweralkyl) or di(hydroxyalkyl)-amino-(loweralkyl).

2. A pharmaceutical composition for enhancing the therapeutic effect of radiation which consists of an effective amount of a compound defined in claim 1 and a non-toxic pharmaceutically acceptable carrier.

3. The compound of claim 1 which is N,N-dimethyl-2-{N-[2-(N-(2-hydroxyethyl)-N-methylamino)ethyl]-N-methylaminosulfonyl}6-nitrobenzamide.

* * * * *